United States Patent [19]
Manset et al.

[11] Patent Number: 5,582,180
[45] Date of Patent: Dec. 10, 1996

[54] COMBINATION THREE-TWELVE LEAD ELECTROCARDIOGRAM CABLE

[75] Inventors: George H. Manset, Woodinville; Neil McIlvaine, Seattle; Randall D. Mills, Woodinville, all of Wash.

[73] Assignee: Physio-Control Corporation, Redmond, Wash.

[21] Appl. No.: 334,845

[22] Filed: Nov. 4, 1994

[51] Int. Cl.$^6$ .................................................. A61B 5/0402
[52] U.S. Cl. ...................... 128/696; 128/639; 439/135; 439/623; 439/652; 439/909
[58] Field of Search ...................... 128/639, 644, 128/695, 696; 439/135, 623, 652, 909

[56] References Cited

U.S. PATENT DOCUMENTS

| | | |
|---|---|---|
| 3,565,055 | 2/1971 | Amarose . |
| 4,121,575 | 10/1978 | Mills et al. . |
| 4,202,344 | 5/1980 | Mills et al. . |
| 4,280,507 | 7/1981 | Rosenberg ............................... 128/696 |
| 4,328,814 | 5/1982 | Arkans . |
| 4,351,343 | 9/1982 | Parrillo et al. ........................... 128/695 |
| 4,353,372 | 10/1982 | Ayer ......................................... 128/640 |
| 4,537,198 | 8/1985 | Corbett . |
| 4,573,474 | 3/1986 | Scibetta . |
| 4,632,121 | 12/1986 | Johnson et al. ......................... 128/639 |

*Primary Examiner*—Lee S. Cohen
*Attorney, Agent, or Firm*—Christensen O'Connor Johnson & Kindness PLLC

[57] ABSTRACT

A bifurcated electrical connector (14) includes a precordial lead connection site (18) and a limb lead connection site (16). A precordial connector (26) can be fitted into the precordial lead connection site (18) and a limb lead connector (32) can be fitted into the limb lead assembly connection site (16). The force required to separate the limb lead connector from the limb lead connection site is greater than the force required to separate the precordial lead connector from the precordial lead connection site. Additionally, a cover flap (75) covers the precordial lead connection site when the precordial electrodes are not in use.

14 Claims, 4 Drawing Sheets

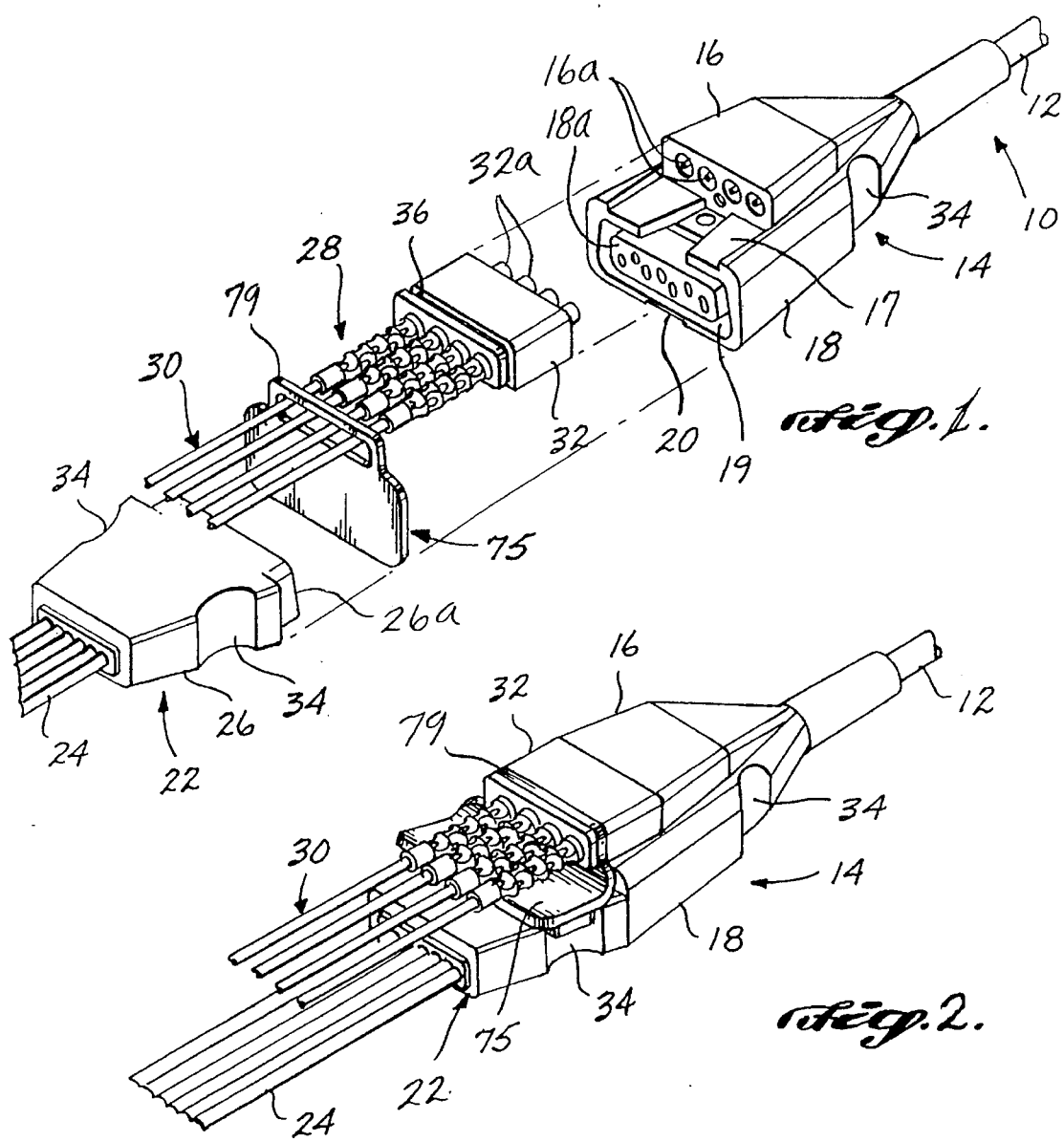
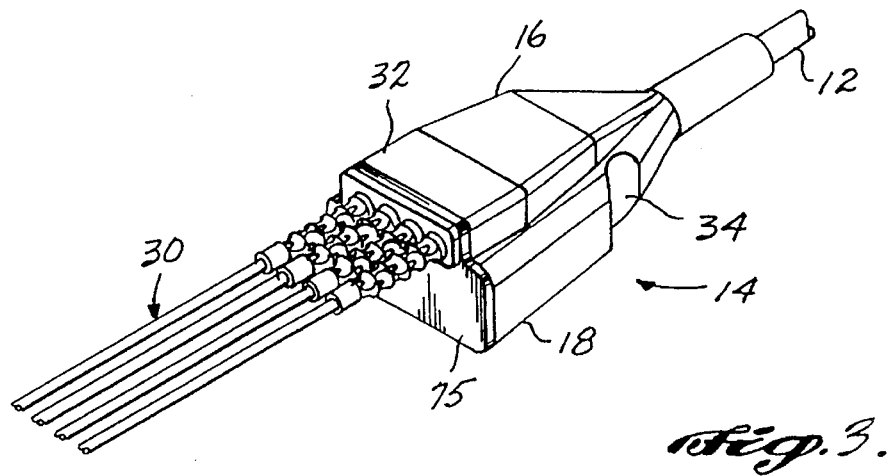

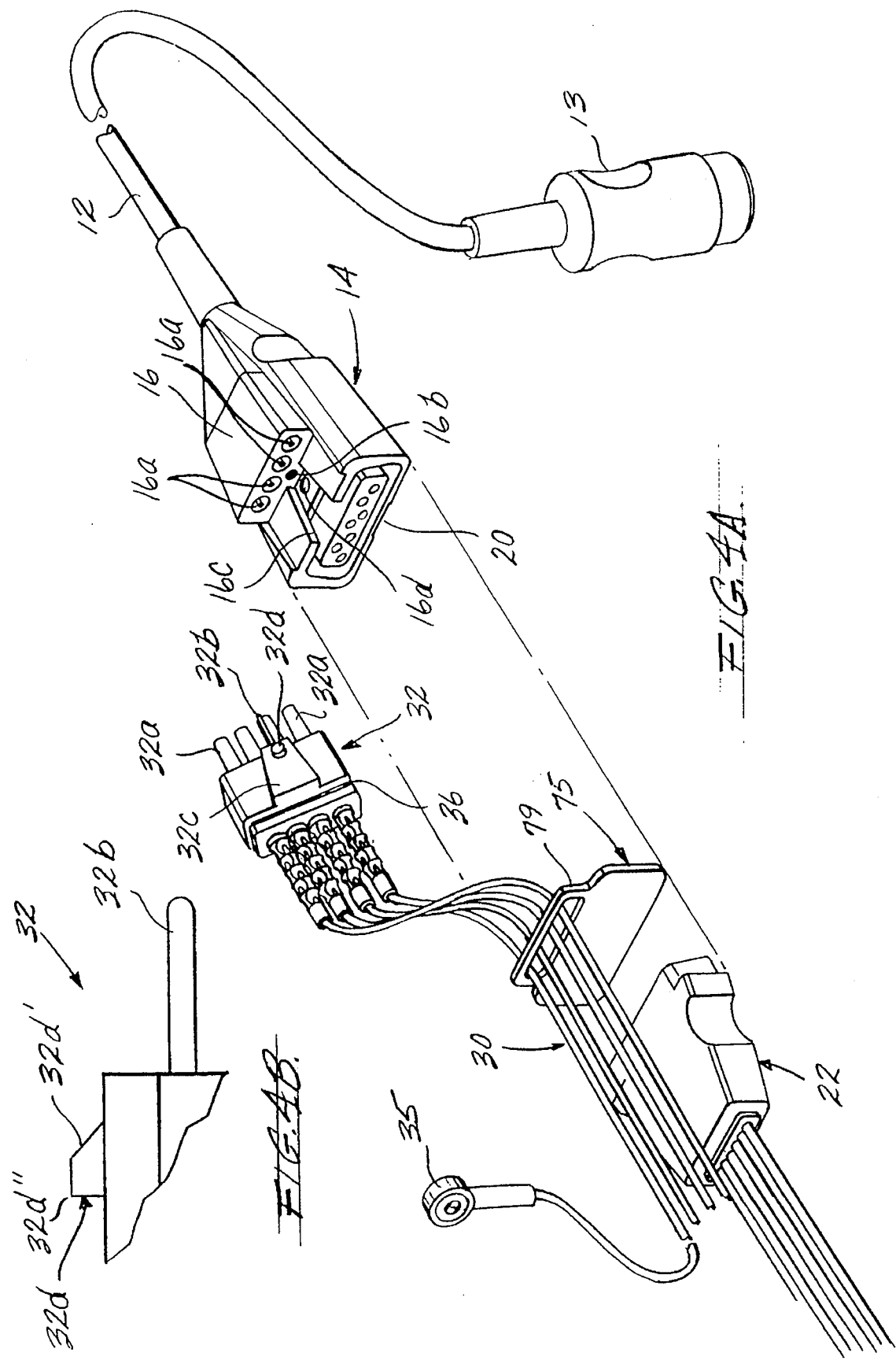

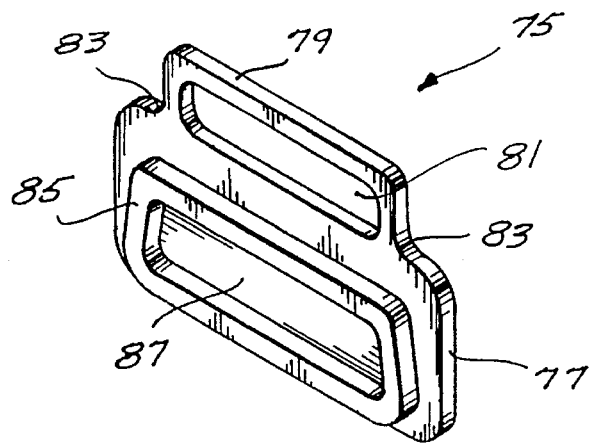
*fig.5.*
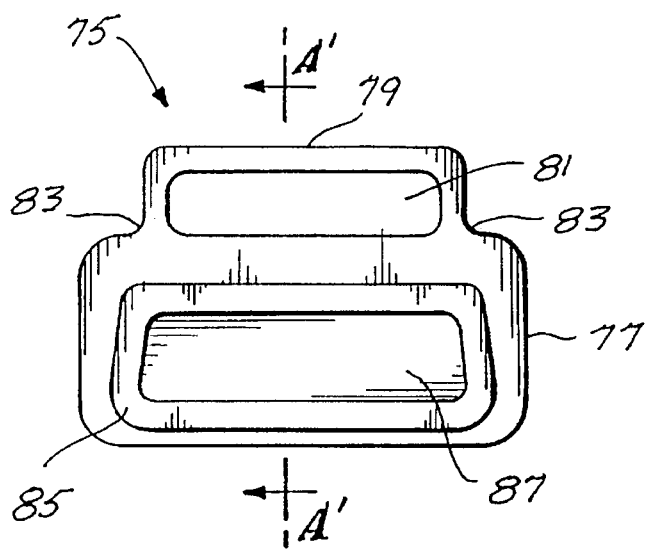 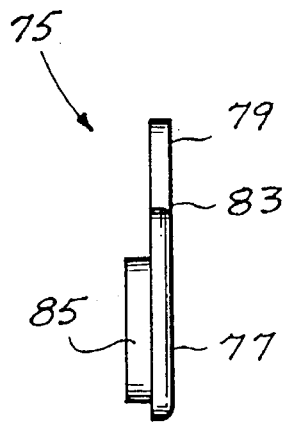
*fig.6.* *fig.7.*
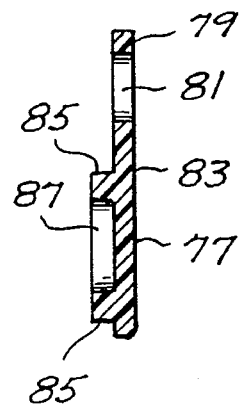
*fig.8.*

COMBINATION THREE-TWELVE LEAD ELECTROCARDIOGRAM CABLE

TECHNICAL AREA OF THE INVENTION

The invention relates to medical cable connectors and, more particularly, to combination limb and precordial electrocardiogram lead assemblies.

BACKGROUND OF THE INVENTION

Many aspects of human physiology can be monitored by electronic monitoring devices. For example, the electrical activity of a patient's brain can be monitored by an electroencephalograph (EEG). Similarly, the electrical activity of a patient's heart can be monitored by an electrocardiograph (ECG). Electronic monitoring by these devices requires the application of one or more sensing electrodes to the patient.

For example, ECG monitoring involves the application of a number of precordial electrodes that are attached to the torso of the patient, and/or limb electrodes that are attached to the limbs of the patient. Electrical activity can be monitored using both the limb electrodes and the precordial electrodes as part of a 12-lead ECG analysis (requiring six electrodes), or using the limb electrodes alone as part of a 3-lead ECG analysis (requiring four electrodes).

Generally, the four limb electrodes are connected via separate electrical conductors to a common limb connector. The six precordial electrodes are connected via separate electrical conductors to a common precordial connector. These connectors are coupled to the ECG monitor. Collectively, the electrodes, conductors and connectors are referred to as lead assemblies.

In most emergency or trauma situations, an attending physician or medical technician is interested in viewing a three-lead ECG signal. The three-lead ECG signal is used in determining what emergency drugs may need to be administered or whether the patient needs to be defibrillated. Twelve-lead ECG signals are most often used in diagnosing the presence or absence of heart disease during nonemergency conditions.

In order to reduce the number of cables that must be connected between the ECG monitor and patient, some ECG lead assemblies are combined such that the four limb electrodes/cable and six precordial electrodes/cable are connected via a separate single multiconductor cable to the ECG monitor. When a standard three-lead ECG signal is desired, the precordial electrodes/cable can be disconnected from the ECG monitor without affecting the connection of the limb electrodes/cable.

With combination lead assemblies, it is important that the connection of the electrodes be intuitive and simple. For example, in emergency situations a physician should not have to guess how the electrodes are connected to the lead assembly. Additionally, there can be problems if the assembly has exposed connection sites. Fluids, such as blood or intravenous medicines, may be accidentally splashed onto an exposed connection site, thereby corroding or short-circuiting conductive elements in the connector. Moreover, dirt particles may accumulate at the exposed connection site, obstructing subsequent connections of the electrode connectors and/or increasing the electrical impedance of the connections. All of these effects may prevent the ECG monitor from correctly sensing electrical activity occurring under the electrodes.

SUMMARY OF THE INVENTION

The present invention provides a combination three-twelve lead electrocardiogram cable. The cable includes a bifurcated electrical connector that includes a precordial lead connection site and a limb lead connection site. The connection sites are formed in a two-tiered relationship, with the limb lead connection site being disposed above the precordial lead connection site. The precordial lead connection site is a trapezoidal socket that mates with a corresponding trapezoidal precordial lead plug. The bifurcated connector and the precordial lead plug include finger grips to facilitate the insertion and removal of the precordial lead plug with the bifurcated electrical connector.

A limb lead plug is designed to be difficult to remove from the bifurcated connector. The limb lead plug terminates at four cylindrical pegs which are received by corresponding bores within the limb lead connection site. The pegs fit tightly in the bores to increase the friction which tends to retain the limb lead plug connected to the bifurcated connector. Additionally, the limb lead plug has a bottom surface with a beveled retainer button that fits in a corresponding recess or depression on the bifurcated connector in order to further secure the limb lead plug within the bifurcated electrical connector.

When a twelve-lead ECG signal is required, both the precordial lead plug and the limb lead plug are inserted into the bifurcated electrical connector. When only a three-lead ECG signal is required, the precordial lead plug is separated from the bifurcated electrical connector. A cover flap is provided to prevent contamination of the precordial lead connection site when the precordial lead plug is not inserted into the bifurcated electrical connector. The cover flap is carded by the limb lead plug.

BRIEF DESCRIPTION OF THE DRAWINGS

The forgoing aspects and many of the attendant advantages of this invention will become more readily appreciated as the same becomes better understood by reference to the following detailed description, when taken in conjunction with the accompanying drawings, wherein:

FIG. 1 is a top perspective of a three-lead/twelve-lead electrocardiogram lead assembly according to the present invention, with parts shown in exploded relationship;

FIG. 2 is a top perspective corresponding to FIG. 1 but with the parts assembled and all components of the lead assembly interconnected;

FIG. 3 is a top perspective corresponding to FIG. 2 but with only the limb leads of the assembly secured to an electrical connector;

FIG. 4A is a top perspective of the lead assembly of FIG. 1 with parts in different positions;

FIG. 4B is a fragmentary, enlarged side elevation of a component of the lead assembly according to the present invention;

FIG. 5 is a top perspective of a first embodiment of a cover flap in accordance with another aspect of the present invention;

FIG. 6 is a front elevation of the cover flap shown in FIG. 5;

FIG. 7 is a side elevation of the cover flap shown in FIG. 6;

FIG. 8 is a transverse section taken along line A'-A" of FIG. 6; and

DETAILED DESCRIPTION OF THE PREFERRED EMBODIMENT

Figure 9:
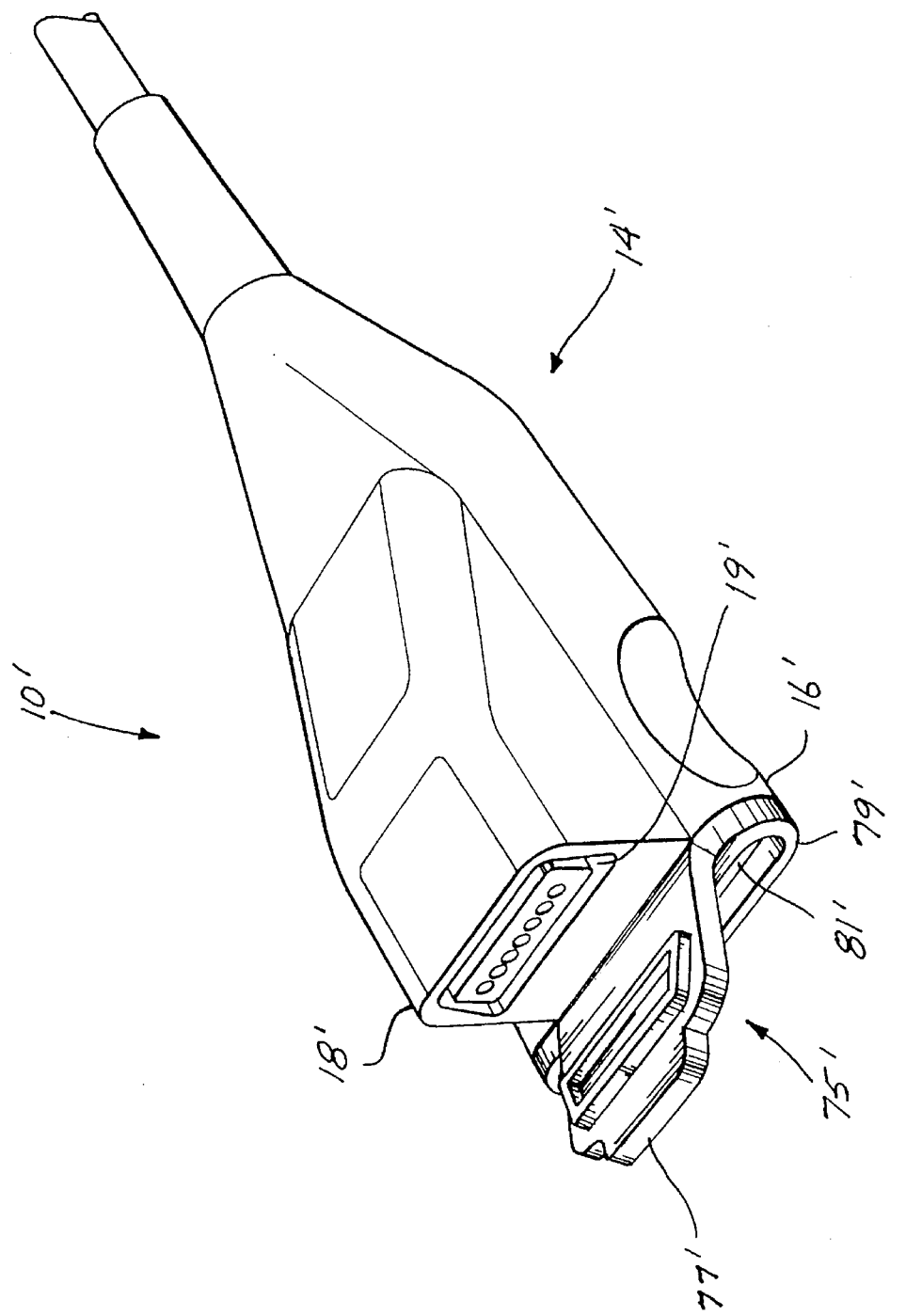
FIG. 9 is a top perspective of an alternate embodiment of a component of a lead assembly according to the present invention.

Turning now to FIG. 1, a three-lead/twelve-lead electrocardiogram lead assembly 10 (hereinafter referred to as a combination lead assembly) according to the present invention includes a bifurcated electrical connector 14, a limb lead assembly 28, a precordial lead assembly 22, and a cover flap 75. The combination lead assembly is divided into two sections. The first section includes the bifurcated electrical connector 14 that is connected to one end of a multiconductor cable 12. The other end of the cable has a remote connector 13 (shown in FIG. 4). Remote connector 13 is designed to mate with a corresponding electrical connector on an electrocardiogram monitor (not shown). The bifurcated electrical connector 14 includes a limb lead connection site 16 and a precordial lead connection site 18, and is molded in a "two tier" relationship with the limb lead connection site being disposed above the precordial lead connection site 18. Additionally, the precordial lead connection site is positioned generally forward of the limb lead connection site 16, thereby creating a step 17 as will be described below. The connection sites 16 and 18 are adapted for receiving mating electrical connectors or plugs on the limb lead assembly 28 and the precordial lead assembly 22, respectively.

The precordial lead assembly 22 includes six shielded precordial leads 24 and a precordial lead plug 26 at one end. Disposed at the other end of each precordial lead 24 is a connector that mates with a corresponding connector on an electrode (not shown). The precordial lead plug 26 includes seven electrical pin contacts (one for each precordial lead 24 and one common ground for the shielding that surrounds the precordial leads) that mate with a corresponding set of electrical socket contacts 18a within the precordial lead connection site 18. The precordial lead plug 26 is designed to be easily inserted into and removed from the bifurcated electrical connector 14. In that regard, both the precordial lead plug 26 and the bifurcated electrical connector 14 include a pair of finger notches 34 that are diametrically opposed on opposite sides of the plug and connector to allow a user to easily remove or insert the precordial lead plug 26 into the bifurcated electrical connector 14. As an additional safety feature, the set of electrical contacts 18a is surrounded by a trapezoidally shaped groove 19. The groove 19 has a base that is wider than the top. The front end portion 26a of the precordial lead plug 26 has a trapezoidal peripheral wall to fit in groove 19, so that the plug cannot be improperly inserted into the bifurcated electrical connector 14 in the wrong orientation, and attempts to insert the plug 26 in the wrong orientation will not damage the electrical contact. Rather, the plug wall will butt against the opposing face of the bifurcated connector. Additionally, the set of electrical contacts 18a and pin contacts within the precordial lead plug 26 are offset or staggered to further prevent the improper connection of the precordial lead plug and the bifurcated connector.

Because three lead electrocardiograms are often read in emergency situations, a limb lead connector or plug 32 is designed to be difficult to remove from the bifurcated electrical connector 14. The limb lead plug 32 is substantially rectangular in cross section and is smaller than the precordial lead plug 26. A set of four limb leads 30 is attached to and extends away from the back of the limb lead plug 32. As can be best seen in FIG. 4A, the four leads 30 terminate inside four corresponding cylindrical protrusions 32a that fit snugly within four electrically isolating cylindrical bores 16a opening through the from face of the limb lead connection site 16. Centrally located within each of the bores 16a is an electrical contact pin that fits in a corresponding electrical contact (not shown) at the center of each cylindrical protrusion 32a. An additional recessed contact socket 16b is provided below the set of bores 16a. Socket contact 16b mates with a corresponding contact pin 32b found on the limb lead connector 32.

The cylindrical protrusions 32a are formed of high friction material, such as a suitable rubber or plastic having some resiliency (for example, polyurethane). Similarly, the material surrounding the corresponding cylindrical bores 16a has a high coefficient of friction. The snug interconnection of the high friction protrusions 32a in the bores 16a firmly holds the limb lead plug 32 connected to the bifurcated electrical connector 14.

To further increase the force required to separate the limb lead connector 32 from the bifurcated electrical connector 14, the limb lead plug has a tapered bottom key 32c with a downward-projecting retainer button 32d. When the limb lead plug 32 is fitted within the limb lead assembly connection site, the key 32c fits within a slot 16c disposed in the step 17 formed by the top surface of the precordial lead connection site 18. A cylindrical bore or depression 16d is centered in the rear end portion of the groove to receive the retainer button 32d. The front edge 32d' of the button 32d is beveled to form a ramp that allows the button to be easily slid toward and into the depression 16d. The rear edge of the button forms an abrupt stop surface 32d" that engages against a corresponding abrupt rear surface of the depression 16d and prevents the limb lead connector 32 from being easily removed from the bifurcated electrical connector 14.

When the physician wants a twelve-lead electrocardiogram, both the limb lead plug 32 and the precordial lead plug 26 are fitted into the bifurcated electrical connector 14, as illustrated in FIG. 2. If the physician wants only a three-lead electrocardiogram, the precordial lead connector 26 is removed from the bifurcated electrical connector 14, as illustrated in FIG. 3.

Returning now to FIG. 1, when only the limb electrodes are desired, the electrical contacts 18a within the precordial electrode assembly connection site 18 are exposed to contaminants. Therefore, the combination lead assembly according to the present invention provides a cover flap 75 to be placed over the electrical connections 18a when the precordial electrodes are not in use. The cover flap in alternative embodiments can be separate from, integrally formed with, or loosely attached to, the bifurcated electrical connector 14 or limb lead plug 28. The cover 75 does not interfere with the attachment of the limb lead plug 28 to the limb lead connection site 16.

FIGS. 5–8 show one embodiment of a cover flap 75 formed in accordance with the present invention. The cover flap 75 includes a precordial cover portion 77, a mounting loop 79, and an engagement rib 85. The precordial cover portion 77, engagement rib 85, and mounting loop 79 are formed of a flexible rubber material such as polyurethane. The flexibility of the material used is important as will be seen in greater detail below. The precordial cover portion 77 is a flat, roughly rectangular element whose width and length are substantially equal to the width and length of the precordial lead assembly connection site 18 of the combination lead assembly 10 (shown in FIGS. 1–4).

The mounting loop 79 secures the cover flap 75 to the limb lead assembly 28. The mounting loop 79 comprises two upwardly extending hinge sections 83 (FIG. 5) connected at the top to form an aperture 81. The two hinge sections 83 provide a flexible and resilient connection between the mounting loop 79 and precordial cover portion 77. The mounting loop is received in a slot 36 found on the limb lead plug 32 in order to secure the cover flap 75 to the limb lead connector. Integrally formed with, and projecting from, the rear face of the precordial cover portion 77 is an engagement rib 85. The engagement rib 85 is included to secure the cover flap 75 to the precordial lead connection site 18 of the bifurcated electrical connector 14 (shown in FIGS. 1–4). The shape of the engagement rib 85 is substantially trapezoidal to fit within the trapezoidal groove 19 found on the bifurcated electrical connector 14. Although the engagement fib is rectangular in cross section, the use of alternative cross section shapes may be used to securely fix the cover portion 77 to the precordial lead connection site 18. For example, the use of a rib having a "dove tail" cross section, in which the width of the rib increases with distance from the cover portion 77, may provide a more secure attachment or "latching" of the cover flap 75 to the precordial lead connection site 18.

The opening of the cover 75 is facilitated by the inclusion of a release notch 20 (shown in FIG. 1) located on the underside of the bifurcated electrical connector 14. In that regard, when the cover flap 75 is in the closed position, the edge of cover portion 77 is generally flush with the front face precordial lead connection site 18, and might be difficult for a user to open. The release notch 20, however, exposes a section of the edge of cover portion 77 allowing the user to catch the cover portion 77 with a finger or fingernail and open cover flap 75. As an alternative, the addition of a tab to the precordial cover portion 77 can accomplish a similar function.

Although the preferred embodiment of the cover flap 75 is engaged to the limb electrode connector 32 by means of a mounting loop 79 that fits with the attachment groove 36 on the limb lead connector 32, the cover flap 75 can also be integrally formed to the limb connector 32. For example, the mounting loop 79 can be fixedly secured, such as by epoxy, to the limb connector 32. Moreover, the cover flap 75 may be directly molded as an integral part of the limb connector 32, in which case the mounting loop 79 is omitted.

In yet another embodiment, the cover 75 can be integrally formed as part of the bifurcated electrical connector of the cable assembly. FIG. 9 shows such an alternative embodiment. A cable assembly 10' is shown with a bifurcated electrical connector 14'. In the bifurcated electrical connector 14', a precordial lead connection site 18' is generally above a limb lead connection site 16'. In this alternative embodiment, a mounting loop 79' may be fixedly attached about the periphery of limb lead connection site 16'. An aperture 81' allows connection site 16' to be accessed by a limb lead connector (not shown). The connection between the mounting loop 79' and the limb lead connection site 16' may be secured, for example, by epoxy. Alternatively, the mounting loop 79' can be omitted and the cover flap 75' molded as part of the limb lead connection site 16'. A precordial cover portion 77' is free to move to a closed position by manually moving the cover portion 77' adjacent the precordial lead connection site 18'.

When only the limb leads are utilized, the precordial cover portion 77' is manually engaged to and covers the precordial lead connection site 18'. However, during 12-lead analysis, where the precordial lead assembly is also utilized, the precordial cover portion 77' is manually pulled away from the precordial lead connection site 18' such that a precordial lead connector can be inserted into the bifurcated electrical connector 14'.

While the preferred embodiment of the invention has been illustrated and described, it will be appreciated that various changes can be made therein without departing from the spirit and scope of the invention. Thus, the scope of the invention is to be determined solely from the following claims.

The embodiments of the invention in which an exclusive property or privilege is claimed are defined as follows:

1. A combination three-twelve lead electrocardiogram cable, comprising a set of limb electrode leads having electrical contacts at corresponding ends thereof;

a limb lead connector disposed at an end of the set of limb electrode leads and supporting said limb electrode lead contacts;

a set of precordial electrode leads having electrical contacts at corresponding ends thereof;

a precordial lead connector disposed at an end of the set of precordial leads and supporting the precordial lead contacts;

a bifurcated electrical connector having a precordial lead connection site and a limb lead connection site that is located above and offset from the precordial lead connection site, the limb lead connection site including a plurality of contacts that mate with the limb lead contacts, the precordial lead connection site including a plurality of contacts that mate with the precordial lead contacts; and a multiconductor cable connected to the bifurcated electrical connector and extending from the contacts of the limb lead and precordial lead connection sites.

2. The combination three-twelve lead electrocardiogram cable of claim 1, wherein the limb lead connector further includes a surface having a retainer button projecting therefrom, and wherein the limb lead connection site on the bifurcated electrical connector further includes a surface adjacent to the limb lead connector surface and having a depression that receives the button to deter separation of the limb lead connector from the limb lead connection site.

3. The combination three-twelve lead electrocardiogram cable assembly of claim 1, wherein said bifurcated electrical connector includes a first pair of finger depressions, said precordial lead connector includes a second pair of finger depressions, said first and second pairs of finger depressions being substantially aligned when said precordial lead connector is connected to said bifurcated electrical connector.

4. The combination three-twelve lead electrocardiogram cable of claim 1, further including a cover flap that mates with said precordial lead connection site, and means for securing the cover flap to the limb lead connector.

5. The combination three-twelve lead electrocardiogram cable of claim 4, wherein the means for securing the cover flap to the limb lead connector comprises a mounting loop extending from the cover flap and defining an aperture for receiving the limb lead connector.

6. The combination three-twelve lead electrocardiogram cable of claim 5, wherein the limb lead connector has a groove for receiving the mounting loop.

7. The combination three-twelve lead electrocardiogram cable of claim 6, wherein the cover flap and the mounting loop are formed by a single piece of rubber material.

8. A combination three-twelve lead ECG cable, comprising:

a unitary bifurcated electrical connector having a limb lead connection site and an adjacent precordial lead connection site;

a limb lead connector manually connectable to and disconnectable from said limb lead connection site; and a precordial lead connector manually connectable to and disconnectable from said precordial lead connection site, said bifurcated electrical connector, limb lead connector, and precordial lead connector including means for securing the limb lead connector in the bifurcated electrical connector so that removal of the limb lead connector from the bifurcated electrical connector requires greater force than removal of the precordial lead connector from the bifurcated electrical connector.

9. A combination three-twelve lead electrocardiogram cable, comprising:

a set of limb electrode leads having electrical contacts at corresponding ends thereof;

a limb lead connector disposed at an end of the set of limb electrode leads and supporting said limb electrode lead contacts in a substantially planar arrangement;

a set of precordial electrode leads having electrical contacts at corresponding ends thereof;

a precordial lead connector disposed at an end of the set of precordial leads and supporting the precordial lead contacts in a substantially planar arrangement;

a bifurcated electrical connector having a precordial lead connection site and a limb lead connection site that is located above and offset from the precordial lead connection site, the limb lead connection site including a plurality of contacts adapted to mate with the limb lead contacts, the precordial lead connection site including a plurality of contacts adapted to mate with the precordial lead contacts, wherein the limb lead connector further includes a surface having a retainer button projecting therefrom, and wherein the limb lead connection site on the bifurcated electrical connector further includes a surface adjacent to the limb lead connector surface and having a depression that receives the retainer button to deter separation of the limb lead connector from the limb lead connection site; and a multiconductor cable connected to the bifurcated electrical connector and extending from the contacts of the limb lead and precordial lead connection sites.

10. The combination three-twelve lead electrocardiogram cable assembly of claim 9, wherein said bifurcated electrical connector includes a first pair of finger depressions, said precordial lead connector includes a second pair of finger depressions, said first and second pairs of finger depressions being substantially aligned when said precordial lead connector is connected to said bifurcated electrical connector.

11. The combination three-twelve lead electrocardiogram cable of claim 10, further including a cover flap that mates with said precordial lead connection site, and means for securing the cover flap to the limb lead connector.

12. The combination three-twelve lead electrocardiogram cable of claim 11, wherein the means for securing the cover flap to the limb lead connector comprises a mounting loop extending from the cover flap and defining an aperture for receiving the limb lead connector.

13. The combination three-twelve lead electrocardiogram cable of claim 12, wherein the limb lead connector has a groove for receiving the mounting loop.

14. The combination three-twelve lead electrocardiogram cable of claim 13, wherein the cover flap and the mounting loop are formed by a single piece of rubber material.

* * * * *